US009366606B1

(12) United States Patent
McPeak et al.

(10) Patent No.: US 9,366,606 B1
(45) Date of Patent: Jun. 14, 2016

(54) FLUID PROCESSING MICRO-FEATURE DEVICES AND METHODS

(71) Applicant: Ativa Medical Corporation, St. Paul, MN (US)

(72) Inventors: Daniel R. McPeak, Minneapolis, MN (US); Ka Man Lee, Minneapolis, MN (US)

(73) Assignee: Ativa Medical Corporation, St. Paul, MN (US)

( * ) Notice: Subject to any disclaimer, the term of this patent is extended or adjusted under 35 U.S.C. 154(b) by 0 days.

(21) Appl. No.: 14/837,697

(22) Filed: Aug. 27, 2015

(51) Int. Cl.
| *G01N 1/38* | (2006.01) |
| *G01N 33/50* | (2006.01) |
| *B01L 3/00* | (2006.01) |
| *B01F 13/00* | (2006.01) |

(52) U.S. Cl.
CPC .............. *G01N 1/38* (2013.01); *B01F 13/0093* (2013.01); *B01L 3/5027* (2013.01); *G01N 33/5094* (2013.01)

(58) Field of Classification Search
CPC ............ B01L 3/5027; B01L 3/502761; B01L 3/502769; B01L 3/502776; B01F 13/0093; B01F 13/0059; B01F 13/0061; B01F 13/0062; B01F 13/0066; G01N 1/38; G01N 33/5094
See application file for complete search history.

(56) References Cited

U.S. PATENT DOCUMENTS

| 6,136,272 | A | 10/2000 | Weigl |
| 6,159,739 | A | 12/2000 | Weigl |
| 6,382,228 | B1 | 5/2002 | Cabuz |
| 6,537,501 | B1 | 3/2003 | Holl |
| 6,549,275 | B1 | 4/2003 | Cabuz |
| 6,557,427 | B2 | 5/2003 | Weigl |
| 6,674,525 | B2 | 1/2004 | Bardell |
| 7,061,595 | B2 | 6/2006 | Cabuz |
| 7,242,474 | B2 | 7/2007 | Cox |
| 7,277,166 | B2 | 10/2007 | Padmanabhan |
| 7,420,659 | B1 | 9/2008 | Cabuz |

(Continued)

FOREIGN PATENT DOCUMENTS

| WO | WO2007076549 A2 | 7/2007 |
| WO | WO2014149310 A1 | 9/2014 |
| WO | WO2015009284 A1 | 1/2015 |

OTHER PUBLICATIONS

Haandel and van der Lubbe, "Handbook Biological Waste Water Treatment: Design and optimisation of activated sludge systems," Chapt. 6, pp. 248-255, 2007.

(Continued)

*Primary Examiner* — Timothy Cleveland
(74) *Attorney, Agent, or Firm* — Fish & Richardson P.C.

(57) ABSTRACT

The present description provides, in some embodiments, an apparatus for mixing a fluid in a circuit having an inlet channel defining a flow path for a fluid including particulate matter, a first reagent channel in fluid communication with the inlet channel and defining a first reagent flow path for a first reagent, the inlet channel and first reagent channel configured to shear the fluid entering the first reagent channel from the inlet channel at a first junction, a shearing channel in fluid communication with the inlet channel and first reagent channel at the first junction, and a diffusion channel in fluid communication with the shearing channel at a second junction, the sheared fluid collectable into the diffusion channel such that the fluid is compressed at least in part by the first reagent to have a thickness close to a diameter of the particulate matter in the fluid.

22 Claims, 9 Drawing Sheets

(56) References Cited

U.S. PATENT DOCUMENTS

| | | | |
|---|---|---|---|
| 7,641,856 | B2 | 1/2010 | Padmanabhan |
| 8,034,296 | B2 | 10/2011 | Cox |
| 8,071,051 | B2 | 12/2011 | Padmanabhan |
| 8,097,225 | B2 | 1/2012 | Padmanabhan |
| 8,323,564 | B2 | 12/2012 | Padmanabhan |
| 8,329,118 | B2 | 12/2012 | Padmanabhan |
| 8,361,410 | B2 | 1/2013 | Padmanabhan |
| 8,383,043 | B2 | 2/2013 | Padmanabhan |
| 8,741,233 | B2 | 6/2014 | Bardell |
| 2004/0043506 | A1 | 3/2004 | Haussecker |
| 2005/0002835 | A1* | 1/2005 | Shaw ............... B01F 3/20 422/130 |
| 2006/0246575 | A1 | 11/2006 | Lancaster |
| 2006/0263888 | A1 | 11/2006 | Fritz |
| 2011/0275111 | A1 | 11/2011 | Pettigrew |
| 2013/0203157 | A1 | 8/2013 | Cheung |
| 2014/0315238 | A1 | 10/2014 | Farrell |

OTHER PUBLICATIONS

Szeto et al., "Microfluidic squeezing for intracellular antigen loading in polyclonal B-cells as cellular vaccines," Sci Rep. 5:10276, 13 pages, May 22, 2015.

Yflow, "Coaxial Electrospinning Machines: R&D Microencapsulation," [retrieved Sep. 11, 2015]. Retrieved from the Internet: <URL: http://www.yflow.com/technology/coaxial_coflowing/>, 4 pages.

* cited by examiner

FLUID PROCESSING MICRO-FEATURE DEVICES AND METHODS

TECHNICAL FIELD

The present specification relates to fluid processing devices, and in particular, microfluidic devices for fluid processing.

BACKGROUND

Fluid analysis of various bodily fluids is commonly used in assessing a patient's health or diagnosing a medical condition. For example, blood cell analysis may provide an indication of a patient's overall health based on the number and characteristics of various types of blood cells, such as red blood cells, white blood cells and platelets. Various manual and automated techniques have been used, including measuring impedance or dynamic light scattering as particles or cells pass through a sensing area. Appropriate analysis requires chemical and physical preparation of cells within a sample which conditions the cells from a natural state to a form more conducive to a particular analysis technique.

Such cell preparation has included mixing fluid samples, such as whole blood, with various reagents. Mixing techniques have included shaking, stirring, and otherwise agitating fluid samples with reagents to create random interactions between particulate matter in the fluid samples, such as blood cells, and reagent fluids. To ensure sufficient interaction, techniques based on random interactions have needed to be performed for at least a minimum period of time so that the fluid sample and its particulate matter can thoroughly mix with the reagent fluids.

SUMMARY

This document generally describes fluid circuits that can provide predictable interactions between a fluid to be analyzed, such as whole blood, and one or more processing agents to facilitate preparation of the fluid for analysis. Such circuits can include a shearing device that shears the fluid to minimize agglomeration of the fluid and a compression device that compresses the fluid. In some implementations, the fluid is compressed to a thickness that is close to or less than a dimension of particulate matter in the fluid. In this way, particulate matter may be in close proximity with one or more processing agents. Such fluidic circuits can also include a channel with sufficient length for particulate matter in the fluid to react with the one or more processing agents before advancing to an analysis location where the fluid may be analyzed by suitable analysis techniques.

In one aspect, an apparatus for mixing a fluid includes a circuit having an inlet channel defining a flow path for a fluid comprising particulate matter, a first reagent channel in fluid communication with the inlet channel and defining a first reagent flow path for a first reagent, the inlet channel and first reagent channel configured to shear the fluid entering the first reagent channel from the inlet channel at a first junction, a shearing channel in fluid communication with the inlet channel and first reagent channel at the first junction, and a diffusion channel in fluid communication with the shearing channel at a second junction. The sheared fluid is collectable into the diffusion channel such that the fluid is compressed at least in part by the first reagent to have a thickness less than 1.5 times greater than a diameter of the particulate matter in the fluid, and the diffusion channel defines a diffusion flow path for the first reagent to interact with, at least, a portion of the particulate matter.

Various implementations may include any, all or none of the following features. A second reagent channel may be in fluid communication with the shearing channel and diffusion channel at the second junction, and define a second reagent flow path for a second reagent. The first and second reagents may be the same. The fluid may be compressed to have a thickness less than a diameter of the particulate matter in the fluid such that at least a portion of the particulate matter extends beyond a thickness of the fluid to contact the first reagent. The inlet channel may have an opening at the first junction having an area between 0.005 $mm^2$ and 0.25 $mm^2$. The opening of the inlet channel at the first junction may have a rectangular cross-section. The ratio of a cross-sectional area of the first reagent channel to a cross-sectional area of the inlet channel at the first junction may be between 1:10 and 1:0.1. The ratio of a cross-sectional area of the inlet channel at the first junction to a cross-sectional area of the diffusion channel at the second junction may be about 1:1. The first junction may be configured such that fluid is sheared along a side wall of the shearing channel. The side wall may be oriented parallel with gravity when the circuit is positioned for use while the fluid is flowing through the inlet channel. The first and second junctions may be separated by a distance between 0.1 mm and 5 mm. The shearing channel and second reagent channel may form an angle between approximately 80 degrees and 190 degrees. The inlet channel, first reagent channel and shearing channel may be coplanar. The first and second reagent channels may include concentric channels. The fluid may be surrounded on at least two opposed sides by the first and second reagents when flowing through the diffusion channel. The fluid may be surrounded on only two opposed sides by the first and second reagents when flowing through the diffusion channel. The fluid may include whole blood and the particulate matter may include blood cells. The apparatus may include a disposable cartridge configured to be inserted into an analyzer device, and the cartridge includes the circuit.

In another aspect, a method of mixing a fluid includes injecting a fluid containing particulate matter into an inlet channel of a circuit, injecting a reagent into first and second reagent channels, the first and second reagent channels defining first and second reagent flow paths, shearing the fluid by the reagent at a first junction at which the fluid inlet channel and the first reagent channel merge into a shearing channel, and compressing the sheared fluid by the regent at a second junction at which the shearing channel and second reagent channel merge into a diffusion channel. In some implementations, the compressed fluid has a thickness less than a diameter of the particulate matter in the fluid, and the diffusion channel provides a length for, at least, a portion of the particulate matter extending into the reagent to react with the reagent.

Implementations can include any, all, or none of the following features. The compressed fluid may have a thickness less than 8 microns. The fluid may exhibit a flow rate ($V_{fluid}$) through the diffusion channel, and 0.05 μL/min < ($V_{fluid}$) < 5000 μL/min. The reagent may exhibit a flow rate ($V_{reagent}$) through the first reagent channel, and 50 μL/min < ($V_{reagent}$) < 5000 μL/min. The fluid may exhibit a flow rate ($V_{fluid}$) through the diffusion channel and the reagent may exhibit a flow rate ($V_{dreagent}$) through the first reagent channel, and $10*(V_{fluid}) < (V_{reagent}) < 1000*(V_{fluid})$. The fluid may be whole blood and the first reagent may be a lysing reagent. The fluid may be whole blood and the first reagent may be a sphereing agent.

In another aspect, an apparatus for mixing a fluid includes a circuit having an inlet channel defining an inlet flow path for whole blood, a first reagent channel in fluid communication with the inlet channel and defining a first reagent flow path for a first reagent, the inlet channel and first reagent channel configured to shear a fluid entering the first reagent channel from the inlet channel at a first junction at which the inlet flow path is oriented 90 degrees relative to the first reagent flow path, a shearing channel in fluid communication with the inlet channel and first reagent channel at the first junction, the fluid sheared along a length of the shearing channel, a second reagent channel in fluid communication with the shearing channel and defining a second reagent flow path for a second reagent, and a diffusion channel in fluid communication with the shearing channel and the second reagent channel at a second junction. The sheared fluid is collectable into the diffusion channel such that the fluid is compressed at least in part by the second reagent to have a thickness less than 1.2 times greater than a diameter of particulate matter in the fluid, the diffusion channel defining a diffusion flow path for first and second reagents to interact with, at least, a portion of the particulate matter extending beyond the thickness of the fluid. The ratio of the inlet channel cross-sectional area to the first reagent channel cross-sectional area at the first junction is between 1:10 and 1:0.1. A distance between the first and second junctions may be between 0.1 mm and 5 mm.

Several features and advantages may be associated with one or more implementations of the systems and methods described herein. For example, reaction between components of a fluid and one or more processing agents is carried out in a controlled manner with close proximity between particulate matter of a fluid and the processing agent. Accordingly, complete mixing may occur with relatively less, or no, reliance on chaotic or random phenomena that could introduce variability from one test to the next. In another example, a fluid may be efficiently processed to minimize a total sample volume that needs to be collected in order to analyze a desired volume of fluid. In a further example, the amount of processing agents required to achieving a complete reaction can be minimized.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings may indicate like elements.

DETAILED DESCRIPTION

Figure 1:
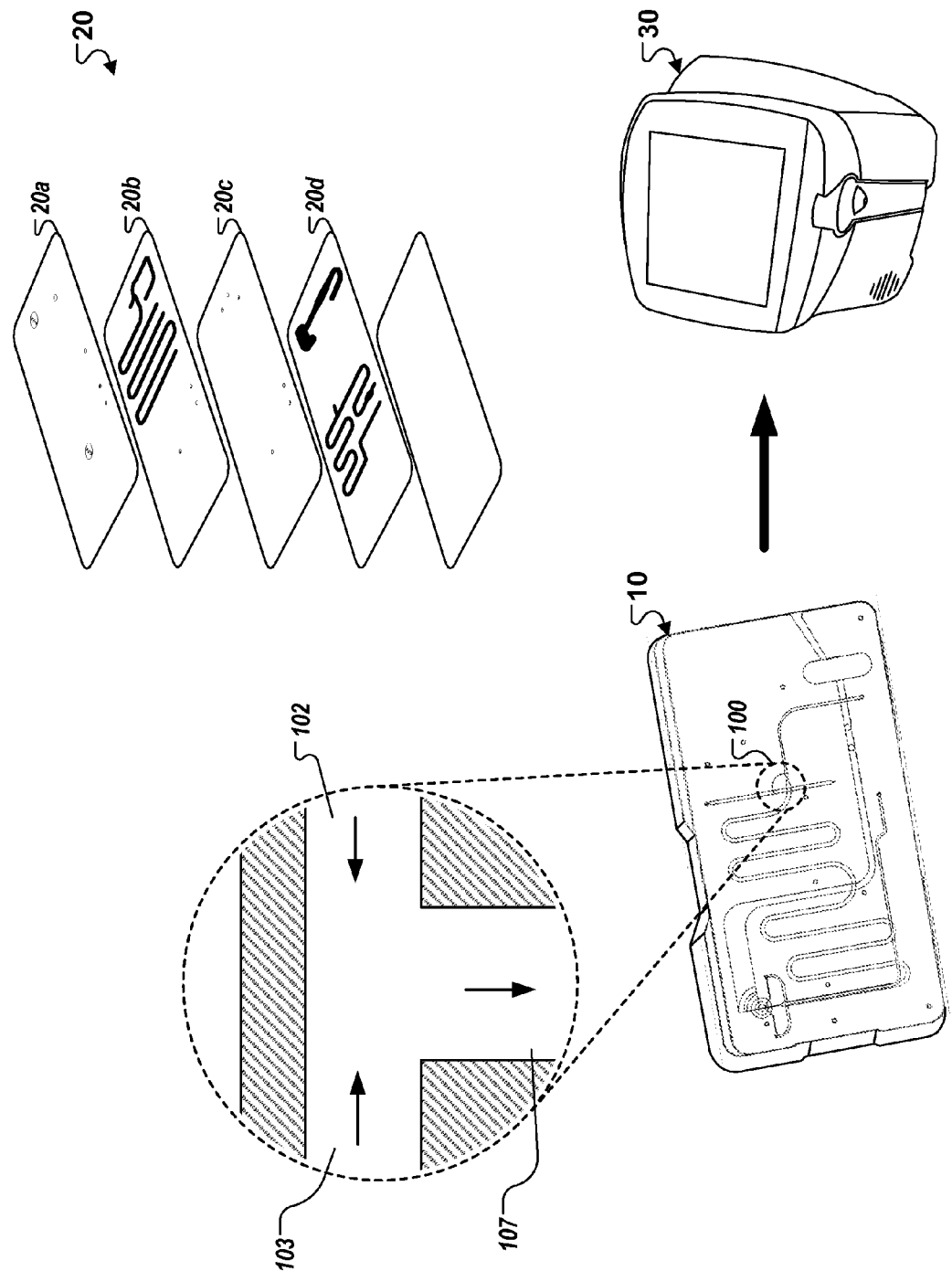
FIG. 1 is a perspective view of an exemplary analyzer system according to one embodiment of the present description.

The present description generally describes devices, systems, designs, and/or techniques suitable for processing and analysis of fluids in small channels. Techniques such as flow cytometry can be used to determine composition and characteristics of a fluid and may use, or benefit from, appropriate preparation of the fluid and particulate matter within the fluid. In some implementations, fluid preparation is achieved by mixing or diluting a fluid with one or more processing agents that are formulated to spur biochemical reactions with the cells. Accordingly, microfluidic flow paths can be configured that result in adequate interaction between a fluid and its constituents and one or more processing reagents in order to prepare the fluid for analysis, as described further herein.

Fluid analysis in micro-environments differs from macroscale analysis and can be challenging due to the behavior of liquids in small channels. In various macro-scale systems, fluid samples combined with processing reagents may be mixed by shaking or agitating, and a resulting aliquot is allowed to stand for an appropriate duration for a desired reaction to occur. The reacted mixture may then be analyzed by traditional techniques. In micro-scale systems, shaking or other mechanical agitation may not effectively result in mixing of a fluid with processing agents. For example, in microenvironments, fluidic movement may be dominated by viscous dissipation which prevents turbulence and/or chaotic advection sufficient to mix fluids with processing agents. As described in greater detail below, fluidic circuits are described that facilitate intimate and sustained contact between fluids and suspended particulate matter, such as blood cells, to allow an appropriate reaction, particularly within micro-scale systems, to occur in advance of analysis. For example, fluidic circuits can create orderly streams of particulate matter, such as blood cells, that are in close proximity with one or more processing agents. Desired interaction between fluid samples and one or more processing reagents can thus be achieved in a predictable and systematic manner, and with limited or no chaotic or random mixing phenomena.

In some implementations, fluidic circuits described herein can address and overcome properties of liquids that present complexities to quantifying particulate matter in small channels. For example, aggregating properties of whole blood can cause the whole blood to become inhomogeneous under low-shear flow conditions. Such behavior may cause errors in cell counting techniques due to non-uniform distribution of cells throughout the microfluidic chambers where cell concentration measurements may be taken. Accordingly, fluidic circuits can include one or more shearing and/or compressing devices that mitigate the tendency for particle-laden fluids, such as whole blood, to become inhomogeneous while flowing through small passages, and to create a consistent flow that may predictably interact with one or more processing agents.

FIG. 1 illustrates components of an exemplary system that uses an example micro-feature to process fluid containing particulate matter. The example system that is depicted includes a cartridge 10 that can receive a fluid, such as whole blood, and that can be inserted into an analyzer device 30 for analysis. The analyzer device 30 can perform various tests on the fluid contained in the cartridge 10 by circulating the fluid within the cartridge 10 in particular ways using fluidic circuits and a dispensing micro-feature 100 that are contained within the cartridge 10. The cartridge 10, which can be disposable (e.g., intended for a single use) and/or reusable (e.g., able to be used multiple times without performance degradation), can be, for example, fabricated by attaching one or more laminated sheets 20 containing the channels of the fluidic circuit.

As described in more detail below, the example micro-feature can include a processing agent channel 102, fluid inlet channel 103, and a diffusion channel 107. The micro-feature can thus provide a fluidic circuit where one or more fluids and one or more processing agents may be brought into contact with one another and react. In some embodiments, the fluid that is inserted into and dispensed from the chamber 110 can be whole blood. Other particle-laden fluids may also be used with the example micro-feature 100.

The cartridge 10 can be a low-cost apparatus that can include different types of fluidic circuits that are formed within the cartridge 10, such as through the multiple sheets 20, for analyzing fluid samples during testing procedures. The cartridge 10 can be fabricated using any of a variety of appropriate manufacturing techniques, such as injection molding, embossing, laser ablation, machining, etching, lamination, and/or various combinations of such techniques. The cartridge 10 can also be manufactured using various materials such as metal, metal alloys, silicon, plastics, polymers, and/or various combinations of such materials.

Fluidic circuits within the cartridge 10 can include various regions to receive, process, and output fluid samples during testing procedures. For instance, the fluidic circuits can include a sample inlet for inserting a fluid sample to be analyzed, multiple reagent inlets involved in the testing procedure, a reaction-sustaining channel where a particular reaction is performed to generate results of the testing procedure, and a circuit outlet where the fluid sample and/or other waste products are dispensed from the cartridge 10. Other fluidic circuits and/or features are also possible.

Fluid may be collected and introduced into the cartridge 10 and/or the micro-feature 100 by any suitable technique. For example, a blood sample may be collected from a patient by a finger prick directly on the cartridge 10 such that the blood sample is collected and directly introduced to the cartridge 10 and/or the micro-feature 100. In other exemplary embodiments, blood may be collected by a finger prick and subsequently introduced to the cartridge 10 and/or the micro-feature 100.

In some implementations, the cartridge 10 can be fabricated using a single laminated sheet. In other implementations, the cartridge 10 can be fabricated using a combination of multiple laminated sheets 20 that can be manufactured separately and/or composed of different materials. For example, the multiple laminated sheets 20 can have different structural properties such as, differing levels of rigidity, elasticity, and/or hardness, to improve the overall strength and durability of the cartridge 10. In another example, the multiple laminated sheets 20 can include individual sheets with different flexibilities such that the flexible layers can be used to form a valve structure within the cartridge 10. In other examples, coating materials can be used for certain layers of laminated sheets that include fluidic circuits that are used to perform reactions with reagents and/or fluid samples.

As shown in FIG. 1, in one example implementation, the multiple laminated sheets 20 includes layers 20a-e, to form the single cartridge 10. In such an implementation, the top and bottom layers, 20a and 20e, respectively, can be made from acrylic to increase the overall durability of the cartridge 10.

The intermediate layers 20b-d can be made from mylar and can include adhesive tacking to bond the multiple laminated sheets 20. The layers 20b and 20d can include fluidic circuits that may be used alternatively and/or in combination to perform sample analysis. For example, the layer 20b can be used to run a fluid sample and layer 20d can be used to run reagent fluid. In another example, the layer 20a can be used to run a sample, and the layer 20b can be used to collect waste products generated from reactions taking place within the fluidic circuit. Other uses, configurations, compositions, properties, and/or arrangements of the layers 20a-e are also possible.

The analyzer device 30 can be a multi-platform point-of-care device capable of performing multiple clinical diagnostic tests using small fluid sample volumes that are injected into the cartridge 10. The analyzer device 30 can be configured to operate with different types disposable cartridges 10 that are adapted to implement various different detection techniques, such as flow cytometry, electrochemistry, colorimetric analysis, and/or imaging of whole blood. For example, in some instances, the analyzer device 30 can be used to perform electrochemical analyses of analytes within a whole blood sample for a basic metabolic panel (BMP). In other instances, the analyzer device 30 can be used to perform flow cytometry assays for detection of particular types of white blood cells such as CD3, CD4, CD8, and C-reactive proteins (CRP), bead-based assays, reflectance spectroscopy for comprehensive metabolic panel (CMP), and/or imaging for determining an erythrocyte sedimentation rate (ESR).

The analyzer device 30 can also include various subsystems that allows the analyzer device 30 to be used as a single-format testing apparatus for performing commonly-occurring blood tests. For example, the analyzer device 30 may include cellular and/or protein analysis subsystems for performing optical/fluorescence flow cytometry and imaging, electrochemical subsystems, and/or photochemical subsystems for performing reflectance/absorption calorimetry and chemiluminescence. In such examples, the subsystems can be physically and/or logically co-housed within a single apparatus such that the analyzer device 30 may be used with different types of cartridges 10 that are specifically designed for various testing procedures. The example micro-feature 100 can be incorporated into various different types of cartridge designs and can be used to dispense fluids to perform various tests by the analyzer device 30.

The analyzer device 30 can also include a user interface, including a display and input features (e.g., touchscreen, keypad, buttons), that allows healthcare professionals or other users to select experimental tests to be performed by the analyzer device 30, to adjust testing parameters, to insert fluid sample information, to view prior or current test results, and/or to transmit the test results over a network. For example, the analyzer device 30 can be used to perform diagnostic tests in low-resource environments, to provide results to onsite medical professional, and to transmit the generated results to a centralized healthcare infrastructure, such as a hospital and/or an electronic medical record system.

For example, the system depicted in FIG. 1 can be used perform cell counting of particular analytes, such as red blood cells, white blood cells, and/or platelet cells within a whole blood sample. For instance, a whole blood sample can be injected into cartridge 10 and received in the chamber 110 as part of the fluid holding and dispensing micro-feature 100. As the whole blood sample is dispensed from the chamber 110 through the outlet port 112, the analyzer device 30 can be used to detect cells that are dispensed through the outlet port 112 and to perform various tests on the dispensed cells. Other uses of the micro-feature 100 and the cartridge 10 by the analyzer device 30 are also possible.

Cartridge 10, analyzer device 30, and/or micro-feature 100 thus provide a compact, efficient and easy to use system that may be readily implemented at a point-of-care location. Such a system may in some embodiments allow a blood sample to be collected, introduced to micro-feature 100, and analyzed, with results available contemporaneously and in an efficient manner. Accordingly, an exemplary system minimizes additional processing steps and associated costs that may otherwise result when a sample must be sent to a dedicated processing laboratory or facility according to traditional analysis techniques. Further, an exemplary system may provide immediate results, increasing the availability of information for a doctor to diagnose and treat a patient, and thus improve overall quality of care.

Figure 2:
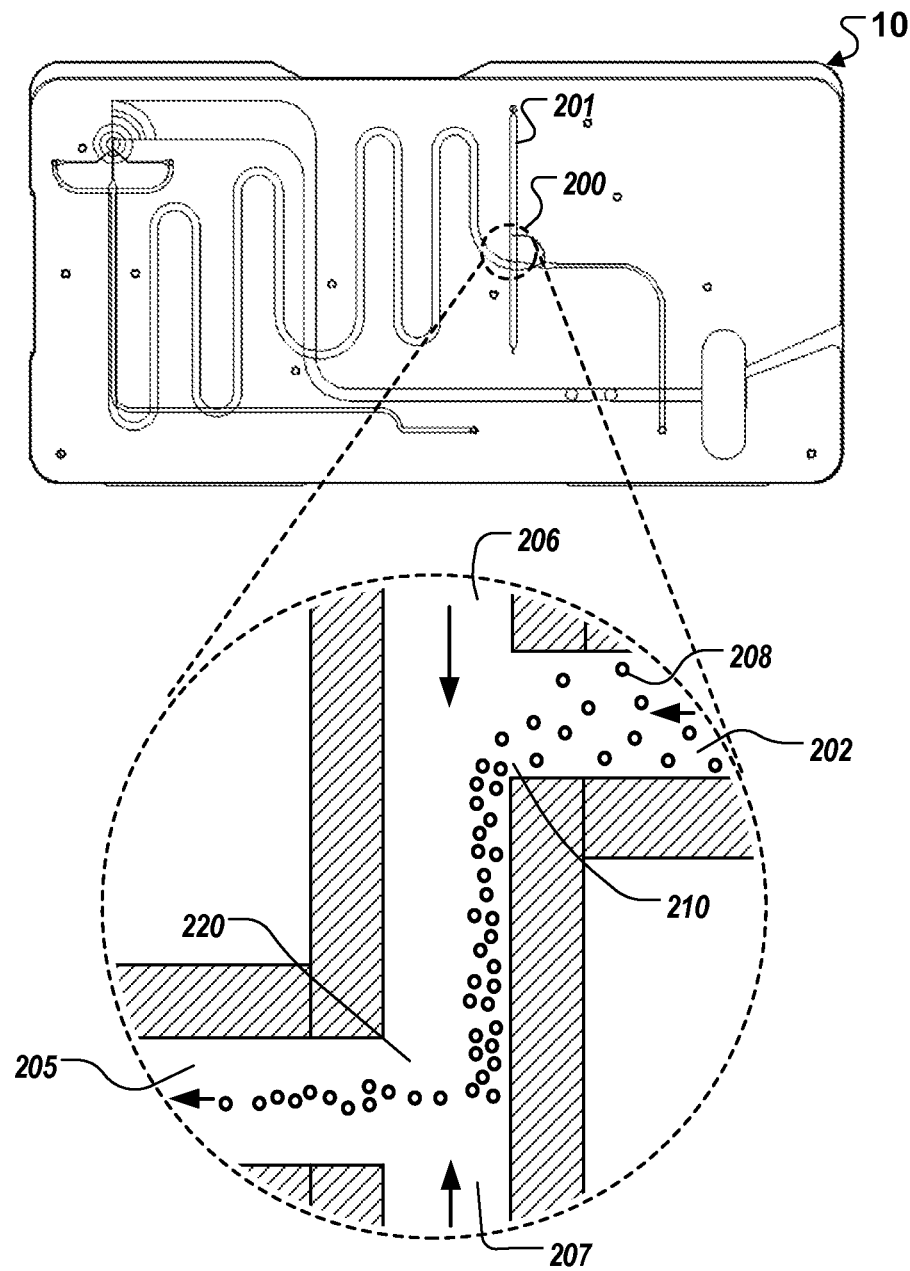
FIG. 2 is a top view of a cartridge including a fluid circuit according to one embodiment of the present description.

Referring to FIG. 2, a top view of an exemplary cartridge 10 is shown including an example fluidic circuit 200 for processing a fluid sample. Circuit 200 defines a flow path for an example fluid 208, which is depicted as including particulate matter (small circles), from an example inlet channel 202 to an example diffusion channel 205, and includes one or more example junctions 210, 220 that allow the fluid 208 to interact with one or more processing agents, such as example processing agents 206, 207. The inlet channel 202 can be in fluid communication with a chamber or fluid source 201 that is configured to control dispensing the fluid 208 into the inlet channel 202. A flow of fluid 208 and one or more processing agents 206, 207 can be affected by pressurizing various portions of cartridge 10 and/or circuit 200 to result in desired flow rates of fluid 208 and one or more processing agents 206, 207. Fluid flows can be selected so that the circuit 200 can effectively process the fluid 208 through controlled reaction with the one or more processing agents 206, 207, as described further herein.

For example, in the depicted implementation in FIG. 2, fluid 208 is initially sheared by processing agent 206 at junction 210 and along a sidewall between junction 210 and 220. Such shearing can alleviate various properties of fluid 208 that may result in fluid 208 being inhomogeneous within circuit 200, such as aggregating properties of whole blood that may cause blood cells (example particulate matter in the fluid 208) to clump together. At junction 220, the example processing agent 207 is introduced to fluid 208 after (or concurrently with) the shearing and, in combination with the flow of the processing agent 206, causes fluid 208 to be compressed. Fluid 208 can be compressed to any of a variety of appropriate dimensions at the junction 220 and/or along the length of the diffusion channel 205, such as being compressed to have a thickness/width that is less than the size of the particulate matter in the fluid 208 (e.g., thickness/width of the fluid 208 compressed to less than the diameter of the particulate matter in the fluid 208), the same as the size of the particulate matter, or to be greater than and within a threshold of the size of the particulate matter (e.g., the fluid 208 is compressed to have a thickness/width that is within a threshold factor (e.g., factor of 1.1×, 1.2×, 1.5×, 2.0× the diameter of the particulate matter) or raw measurement (e.g., within 1 µm, 2 µm, 4 µm, 6 µm, 8 µm, 12 µm, 16 µm) of the size of the particulate matter in the fluid 208). By compressing the thickness/width of fluid 208, circuit 200 can allow for the particulate matter in fluid 208 to interact with processing agents 206 and/or 207 in a predictable and systemic manner without agitation, such as shaking or mixing.

After the fluid 208 is sheared and compressed, it can be used in any of a variety of ways. For example, the fluid 208 can be transported through various channels to an analyzer location, such as a transparent window, where fluid 208 and/or particulate matter suspended in fluid 208 can be quantified or otherwise analyzed.

The example circuit 200 that is depicted in FIG. 2 can be modified in any of a variety of appropriate ways to permit the same or substantially similar processing of fluid 208 and its particulate matter to be achieved. For example, although junctions 210 and 220 depict right angles at which processing agents 206 and 207 are introduced to fluid 208, non-right angles for the junctions can be used as well. In another example, the channels and junctions that are depicted can be differently sized relative to each other, and can be shaped differently along portions of their lengths (e.g., curved portions of the channels). Although not depicted, some surfaces and/or sidewalls of the channels and/or junctions may have different textures, coatings, and/or surface features that assist in the shearing and compressing of fluid 208.

Figure 3:
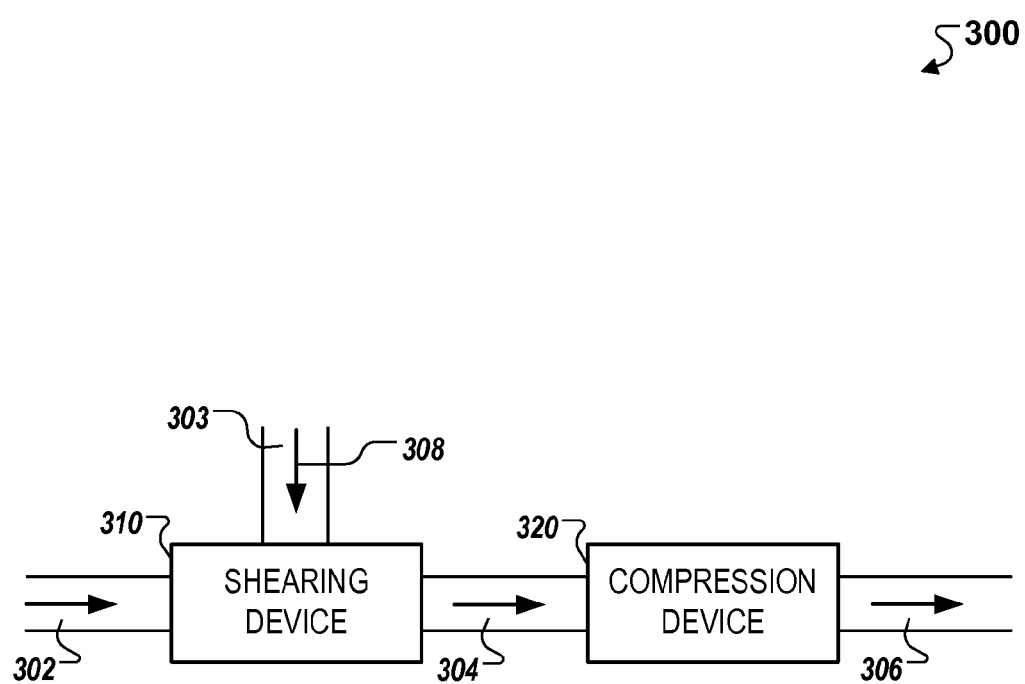
FIG. 3 is a schematic diagram of an exemplary circuit according to one embodiment of the present description.

Referring to FIG. 3, a schematic of an exemplary circuit 300 is shown including an example inlet channel 303, an example reagent channel 302, an example shearing channel 304, and an example diffusion channel 306. Circuit 300 defines a flow path for an example fluid 308 including suspended particulate matter such that fluid 308 travels through a shearing device 310 and a compression device 320 while interacting with one or more processing agents 306 in advance of the fluid 308 being, for example, analyzed at an analyzing location (not shown).

The shearing device 310 is configured to shear fluid 308 so that clumping or other agglomeration of particulate matter in fluid 308, such as naturally occurring agglomeration of blood that can occur over time, is minimized. Shearing channel 304 defines a flow path for shearing fluid 308 to travel to a compression device 320. The junction 210 described above with regard to FIG. 2 is an example of a shearing device 310.

The compression device 320 is configured to compress fluid 308 at least in part by a processing agent such that fluid 308 is compressed to a thin stream or ribbon having a thickness similar to or less than a diameter or other dimension of particulate matter suspended in fluid 308. That is, at least one component of fluid 308 may be compressed while relatively more rigid particulate matter is not. In this way, particulate matter may be brought into close or direct contact, such as by the particulate matter extending beyond one or more dimensions of the compressed fluid 308, with one or more processing agents. Direct contact may be maintained over a sufficient length of diffusion channel 306 to allow time for a desired reaction to occur in preparation of fluid 308 reaching, for example, an analyzing location where fluid 308 is analyzed by flow cytometry or other suitable techniques, as described in greater detail herein. In some implementations, shearing device 310 can be provided simultaneously with, or at the same location as, compression device 320.

The fluid 308 can be any fluid suitable for processing in a fluidic circuit. In some embodiments, fluid 308 is blood, such as whole blood, and includes blood cells such as red blood cells, white blood cells, platelets, and other components. Other fluids can also be used, such as bone marrow aspirate, spinal fluid, serous cavity fluid, urine, other bodily fluids, other fluids including suspended particulate matter, and other fluids suitable for processing in a fluidic circuit.

The circuit 300 allows fluid 308 to interact with one or more processing agents before reaching, for example, an analyzing location where fluid 308 will be analyzed. In some embodiments, processing agents can include one or more reagents such as lysing agents, sphereing agents, sheathing agents, dyes, diluents, other suitable processing agents and/or combinations thereof suitable for interaction with fluid 308 to appropriately condition the fluid 308 and it particulate matter for analysis.

In some embodiments, the fluid 308 is analyzed by flow cytometry techniques, and can be used to detect cell concentration and characteristics, such as particle type, volume ratios, and dimensions and/or other characteristics or information. In various exemplary embodiments, the fluid 308 can be analyzed using dynamic light scattering techniques such as Mie-scattering, impedance techniques such as Coulter-impedance, other suitable techniques for analyzing particulate-laden fluids, and/or suitable combinations thereof.

The circuit 300 can be included in any suitable system for analyzing a fluid. In some embodiments, the circuit 300 is provided in a cartridge, such as disposable cartridge 10 described above with reference to FIGS. 1 and 2. The fluid 308 can be injected into a disposable cartridge, which can be inserted into or otherwise made accessible to an analyzer device for analyzing the fluid injected into the cartridge. The analyzer device may control the flow of fluid 308 and/or one or more processing agents 306 through circuit 300, process fluid 308, and output information related to the analyses performed, as further described herein. In other exemplary embodiments, the circuit 300 can be reusable, and/or included as a component of an analyzer device.

Figure 4:
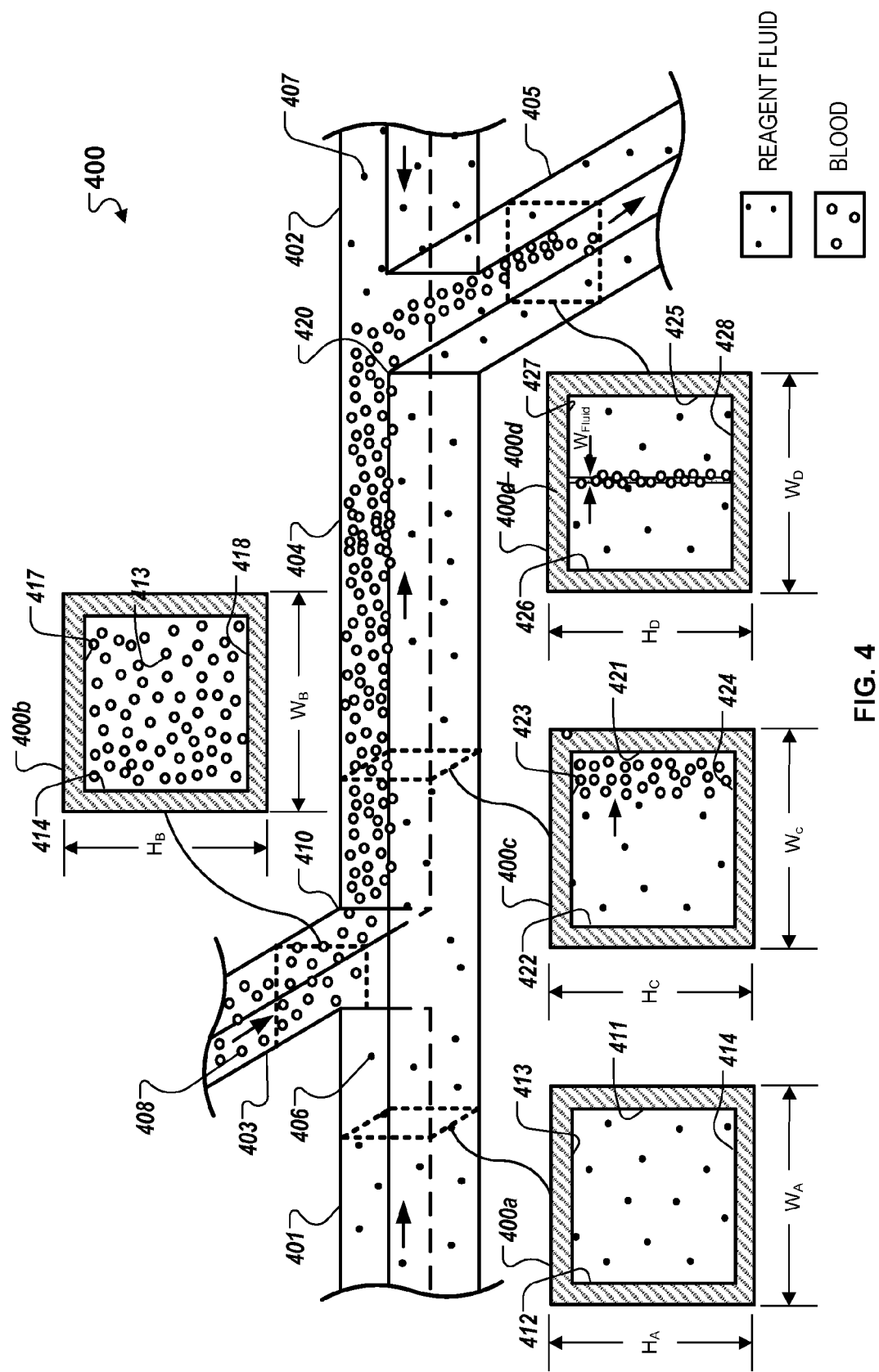
FIG. 4 is a perspective view of an exemplary circuit according to one embodiment of the present description including first and second junctions.

Referring to FIG. 4, an exemplary circuit 400 is shown for processing a flow of fluid. Circuit 400 includes a first reagent channel 401, a second reagent channel 402, an inlet channel 403, a shearing channel 404, and a diffusion channel 405. Circuit 400 defines a flow path for a fluid 408 containing particulate matter, such as whole blood including suspended red and white blood cells and platelets. Fluid 408 may flow from inlet channel 403, through shearing channel 404, and into diffusion channel 405. Circuit 400 thus provides a flow path for a volume of fluid 408 that can result in sustained contact between particulate matter of fluid 408 and one or more processing agents.

Circuit 400 may have any geometric configuration suitable for processing a flow of fluid including suspended particulate matter. In an exemplary embodiment, first reagent channel 401 and inlet channel 403 intersect and are in fluid communication at a first junction 410. First reagent 406 and fluid 408 may flow through first reagent channel 401 and inlet channel 403, respectively, and contact each other at first junction 410 while entering shearing channel 404. Second reagent channel 405 defines a flow path for a second reagent 407 and is in fluid communication with shearing channel 404 at a second junction 420. First reagent 406 and fluid 408 flowing through shearing channel 404 interact with second reagent 407 at second junction 420. Fluid 404 is then collected into diffusion channel 405 by first and second reagents 406, 407, for example, such that fluid 408 is compressed by first and/or second reagents 406, 407. At least one component of fluid 408 may be compressed while relatively more rigid particulate matter is not compressed, resulting in fluid 408 forming a stream or ribbon having fluid thickness that is similar to or less than a diameter or other dimension of particulate matter suspended in fluid 408. Particulate matter of fluid 408 may thus extend out of a fluid stream and into first and second reagents 406, 407, and directly contact first and/or second reagents, for example, such that a controlled reaction may occur as fluid 408 travels through diffusion channel 405.

Cross-section 400a shows a cross-section of first reagent channel 401 upstream of first junction 410 including first and second sidewalls 411, 412 and top and bottom walls 413, 414. First reagent channel 401 thus has a width (WA) between first and second side walls 411, 412 and a height (HA) between top and bottom walls 413, 414 and defines a cross-sectional area of cross-section 400a. Cross-section 400b shows a cross-section of inlet channel 403 upstream of first junction 410 including first and second side walls 415, 416 and top and bottom walls 417, 418. Inlet channel 403 thus has a width (WB) between first and second side walls 415, 416 and a height (HB) between top and bottom walls 417, 418 and defines a cross-sectional area of cross-section 400b. Cross-section 400c shows a cross-section of shearing channel 404 upstream of second junction 420 including first and second side walls 421, 422 and top and bottom walls 423, 424. Shearing channel 404 thus has a width (WO between first and second side walls 421, 422 and a height (Hc) between top and bottom walls 423, 424 and defines a cross-sectional area of cross-section 400c. Cross-section 400d shows a cross-section of diffusion channel 405 downstream of second junction 420 including first and second side walls 425, 426 and top and bottom walls 427, 428. Diffusion channel 405 thus has a width (WD) between first and second side walls 425, 426 and a height (HD) between top and bottom walls 427, 428 and defines a cross-sectional area of cross-section 400d.

In an exemplary embodiment, each channel defines a square or rectangular channel. In other exemplary embodiments, the channels may have circular, elliptical, asymmetrical, or any other suitable cross-sectional shape or suitable combinations thereof, and may be described by any suitable dimensions. The dimensions, geometry, configuration and flow characteristics of circuit 400 may be selected to affect interaction between first and second reagents 406 and fluid 408 at first and second junctions 410, 420, as described further herein.

Circuit 400 and/or first junction 410 may be configured to result in shear of fluid 408 as fluid 408 exits fluid inlet channel 403 and enters shearing channel 404 at first junction 410. In the exemplary embodiment shown in cross-section 400c, a relatively thin strip of fluid 408 travels along sidewall 414, while a remaining portion of cross-section 400c is occupied by first reagent 406. Shearing of fluid 408 may continue along first sidewall 421 as fluid 408 flows through shearing channel 404. In some embodiments, surface properties of sidewall 404a, such as surface roughness, may further contribute to shearing of fluid 408. Shearing channel 404 may have any suitable length, and for example may have a length between 0.1 mm and 20 mm, 0.1 mm and 5 mm, or about 1.8 mm, between first and second junctions 410, 420.

In various exemplary embodiments, fluid 408 entering and/or traveling through shearing channel 404 undergoes a shear between $1\ s^{-1}$ and $10,000\ s^{-1}$, $40\ s^{-1}$ and $1000\ s^{-1}$, or about $100\ s^{-1}$. Such shear separates agglomeration of blood cells that can naturally occur in blood over time and that could otherwise disrupt predictable fluid flow, while avoiding damaging cells or particulate matter of fluid 410 that could result from excessive shearing.

A magnitude of shear on fluid 408 can be controlled in part based on the relative dimensions of first reagent channel 401 and inlet channel 403, the relative flow rates of first reagent 406 and fluid 408, and other characteristics of first reagent channel 401, inlet channel 403, first reagent 406, and fluid 408. In various exemplary embodiments, cross-sectional area of first reagent channel 401 proximate first junction 410 is between $0.001\ mm^2$ and $1\ mm^2$, $0.005\ mm^2$ and $0.25\ mm^2$ or about $0.03\ mm^2$, and a cross-sectional area of inlet channel 403 proximate first junction 410, for example at an opening of inlet channel 403, is between $0.001\ mm^2$ and $1\ mm^2$, $0.005\ mm^2$ and $0.25\ mm^2$ or about $0.0375\ mm^2$. Accordingly, a ratio of a cross-sectional area of first reagent channel 401 to a cross-sectional area of inlet channel 403 may be between 1:30 and 1:0.03, 1:10 and 1:0.1, or about 1:1.125. Such dimensions provide a desired level of shear over a range of relative flow rates of first reagent 406 and fluid 408.

Sheared fluid 408 traveling through shearing channel 404, for example along sidewall 421, is routed into diffusion channel by second reagent 407 at second junction 420, and compressed to promote interaction with first and/or second reagents 406, 407. In the exemplary embodiment of FIG. 4, fluid 408 is collected by first and second reagents 406, 407 into diffusion channel 405 such that a stream or ribbon of fluid 408a extends vertically through a central region of diffusion channel 405. The dimensions of fluid 408 flowing in diffusional channel 405 may be predicted and controlled based on the flow rates of fluid 408 and first and second reagents 408, and the dimensions of diffusion channel 405. Circuit 400 and diffusion channel 405 thus allow flow rates to be selected and provided through diffusion channel 405 that result in a desired thickness of fluid 408 that is similar to or less than a diameter or other dimension of particulate matter suspended in fluid 408.

In various exemplary embodiments, a width ($W_{fluid}$) of fluid 408a is related to a product of a width (WD), for example, of diffusion channel 405 and the ratio of the volumetric flow rate ($V_{fluid}$) of fluid 408 to the total volumetric flow rate ($V_{total}$) through diffusion channel 405, including the volumetric flow rate ($V_{fluid}$) of fluid 408 and the volumetric flow rate ($V_{reagent}$) of first and second reagents 406, 407. For example, a width of fluid 408 ($W_{fluid}$) may be calculated based on equation (1):

$$W_{fluid} \approx W_D * \left( \frac{\dot{V}_{fluid}}{\dot{V}_{reagent} + \dot{V}_{fluid}} \right) \quad (1)$$

Equation (1) may be used to select and deliver a volumetric flowrate of reagent resulting in a width ($W_{fluid}$) of fluid 408a that is similar to or less than a diameter or dimension of particulate matter suspended in fluid 408. A diameter of particulate matter may be any suitable dimension of particulate matter and may refer to a width, thickness, or other suitable dimension selected to promote direct contact between the particulate matter and first and/or second reagent. In an exemplary embodiment, fluid 408 is whole blood containing red blood cells having a diameter of 6 to 8 μm. In various exemplary embodiments, flow rates of fluid 408 and first and second reagents 406, 407 may be selected such that width ($W_{fluid}$) is less than 6 to 8 μm. In various exemplary embodiments, diffusion channel 405 has a width ($W_D$) between 25 μm and 5000 μm, 100 μm and 2500 μm, 150 μm and 1000 μm, or about 200 μm. The volumetric flow rate ($V_{reagent}$) of first and second reagents 406, 407 may be between 50 μL/min and 5000 μL/min, 100 μL/min and 3000 μL/min, or about 2000 μL/min, the volumetric flow rate ($V_{fluid}$) of fluid is between 0.05 μL/min and 50 μL/min, 1 μL/min and 25 μL/min, or about 5 μL/min, and volumetric flow rate ($V_{reagent}$) is between 10 and 1000, 25 and 500, or about 75 times greater than a volumetric flow rate of ($V_{fluid}$) flowing through diffusion channel 405. Such ranges result in a suitable width of fluid 408 in diffusion channel 405 over a range of sizes and configurations of diffusion channel 405.

Fluid 408 can be compressed to any of a variety of appropriate dimensions such that width (Wfluid) is less than the size of the particulate matter in the fluid 408 (e.g., less than the diameter of particulate matter in fluid 408), the same as the size of particulate matter, or greater than and within a threshold of the size of the particulate matter (e.g., within a threshold factor (e.g., factor of 1.1×, 1.2×, 1.5×, 2.0×, 2.5×, 3.0× the diameter of the particulate matter) or raw measurement (e.g., within 1 μm, 2 μm, 4 μm, 6 μm, 8 μm, 12 μm, 16 μm, 24 μm) of the size of the particulate matter in fluid 408). In various exemplary embodiments, such ranges allow width ($W_{fluid}$) to be thin enough that a time required for diffusion is small as compared to chemical reaction.

Diffusion channel 405 provides a length for at least a portion of the particulate matter that may extend into, and directly contact, first and/or second reagents 406, 407 to react with first and second reagents 406, 407. A length of diffusion channel may be selected based on characteristics of fluid 408 and first and second reagents 406, 407 reacting with particulate matter of fluid 408. In various exemplary embodiments, diffusion channel 405 defines a flow path having a length between 1 mm and 10,000 mm, 10 mm and 1000 mm, or about 140 mm, between second junctions 420 and an outlet downstream of second junction 420, such that the length allows sufficient time for fluid particles to react with the first and/or second reagents 406, 407.

Close proximity between particulate matter of fluid 408 and first and/or second reagent 406, 407 provides several features and advantages in processing fluid 408. Rapid reaction between particulate matter of fluid 408 and first and/or second reagents 406, 407 is promoted without reliance on advective or chaotic phenomena. Further, because advective or chaotic phenomena are not required, consistent and highly repeatable reactions are promoted with reduced variability that could otherwise result. Accordingly, circuit 400 provides an orderly flow of cells that may react over a relatively shorter and more predictable length. A physical length of diffusion channel 405, and a time for fluid 408 to appropriately react with first and/or second reagents, may be relatively shorter as compared to systems that do not promote close proximity between particulate matter of fluid 408 and one or more reagents 406, 407.

Furthermore, circuit 400 results in a more efficient use of fluid 408 and first and second reagents 406, 407. A smaller total volume of fluid 408 is needed in order to analyze a particular volume of fluid 408 due to the precisely controlled flow and interaction with one or more processing agents within circuit 400. That is, while certain test protocols may specify analysis of a particular volume of fluid, circuit 400 facilitates analysis of the particular volume while requiring that less total volume be collected and introduced into circuit 400 as compared to some traditional techniques. In an exemplary embodiment, a total volume of fluid 408 collected from a patient, for example by a finger prick, may be between 10 microliters and 200 microliters, 20 microliters and 150 microliters, or about 40 microliters.

In an exemplary embodiment, some or each of first and second reagent channels 401, 402, inlet channel 403, shearing channel 404, and/or diffusion channel 405 are coplanar. For example, respective top walls 413, 417, 423, 427 and/or bottom walls 414, 418, 424, 428 are coplanar. A coplanar relationship of various channels of circuit 400 can facilitate uniform and predictable flow through circuit 400. For example, a coplanar relationship between first reagent channel 401 and inlet channel 403 at first junction 410 facilitates consistent flow of fluid from inlet channel 408 and into shearing channel 404, and may minimize the formation of bubbles or discontinuities. In some exemplary embodiments, a consistent flow of fluid 408 facilitates fluid 408 flowing substantially over an entire sidewall 421 between top and bottom walls 423, 424, as shown in cross-section 400c. That is, fluid 408 flows along and substantially covers entire sidewall 421, rather than flowing only along a portion of sidewall 421. In an exemplary embodiment, flow of fluid 408 and/or one or more reagents 406, 407 may be characterized by Hele-Shaw flow, in which the respective fluid streams are relatively predictable and controlled.

In various exemplary embodiments, each of first and second reagent channels 401, 402, inlet channel 403, shearing channel 404, and/or diffusion channel 405 are oriented substantially orthogonal to the force of gravity when circuit 400 is positioned for use and fluid is flowing through circuit 400. In such embodiments, fluid 408 is sheared along sidewall 421 that is oriented substantially parallel with gravity, and is collected into diffusion channel 405 by first and second reagents 401, 402 flowing substantially perpendicular to gravity.

While the exemplary embodiment of circuit 400 is shown having one inlet channel 403 and first and second reagent channels 406, 407, any suitable number of inlet channels and reagent channels may be provided. Further, first and second reagents 406, 407 provided in on or more reagent channels may be the same or different reagents. In some exemplary embodiments, circuit 400 includes one, two, three, or more than three inlet channels and one, two, three, or more reagent channels that may process a fluid separately or along a common diffusion channel, such as diffusion channel 405. Respective flow rates may be provided as described herein to provide one or more fluid streams having a width that is similar to or less than a diameter or other dimension of suspended particulate matter such that the particulate matter may contact and react with one or more reagents.

Furthermore, first and or second junctions 410, 420, may be configured such that fluid 408 flows through any suitable portion of diffusion channel 405. In the exemplary embodiment of FIG. 4, fluid 408 forms a ribbon or stream at central region of diffusion channel 405 extending between top and bottom walls 423, 424, as viewed in cross-section 400d, such that fluid 408 is surrounded on two opposed sides by first reagent 401 and second reagent 402, respectively. In other exemplary embodiments, fluid 408 may flow along one or more walls of diffusion channel 405, such that fluid 408 is fluid surrounded by first and or second reagent 406, 407 on only one side, or may flow through a central region of diffusion channel not extending between top and bottom walls 423, 424 such that fluid 408 is surrounded on all sides by first and/or second reagents 406, 407.

Figure 5:
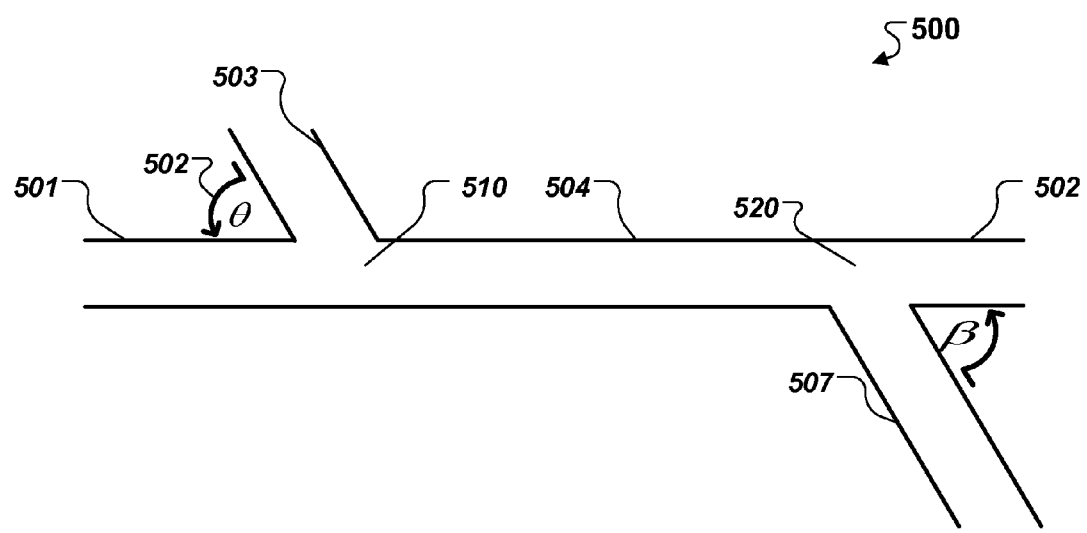
FIG. 5 is a top view of an exemplary circuit according to one embodiment of the present description.

An exemplary circuit may have any configuration that promotes suitable flow of fluid. For example, junctions between two or more portions of a circuit may define any suitable angle. Referring to FIG. 5, an exemplary circuit 500 is shown including a first junction 510 and a second junction 520 that form non-right angles. For example, a first reagent channel 501 and inlet channel 503 define flow paths forming an angle (θ) at first junction 510. Similarly, second reagent channel 502 and diffusion channel 507 define flow paths forming an angle (β) at second junction 520. In various exemplary embodiments, angles (θ) and (β) may be varied to result in desired flow characteristics suitable for a particular application. For example, angles (θ) and/or (β) may be between 15° and 270°, 30° and 210°, 80° and 190° or any suitable angle. Similarly, shearing channel 504 may be oriented in any suitable configuration between first and second junctions 510, 520.

In some exemplary embodiments, angle (θ) and/or (β) may be approximately 90° (for example within 5 degrees), such that a flow path defined by first reagent channel 501 is approximately perpendicular to a flow path defined by inlet channel 503, and a flow path defined by second reagent channel us approximately perpendicular to a flow path defined by a diffusion channel 507. Further, fluid 508 may turn approximately 90 degrees at first junction 510 to enter shearing channel 504, and approximately 90 degrees at second junction 520 to enter diffusion channel 507.

Figure 6:
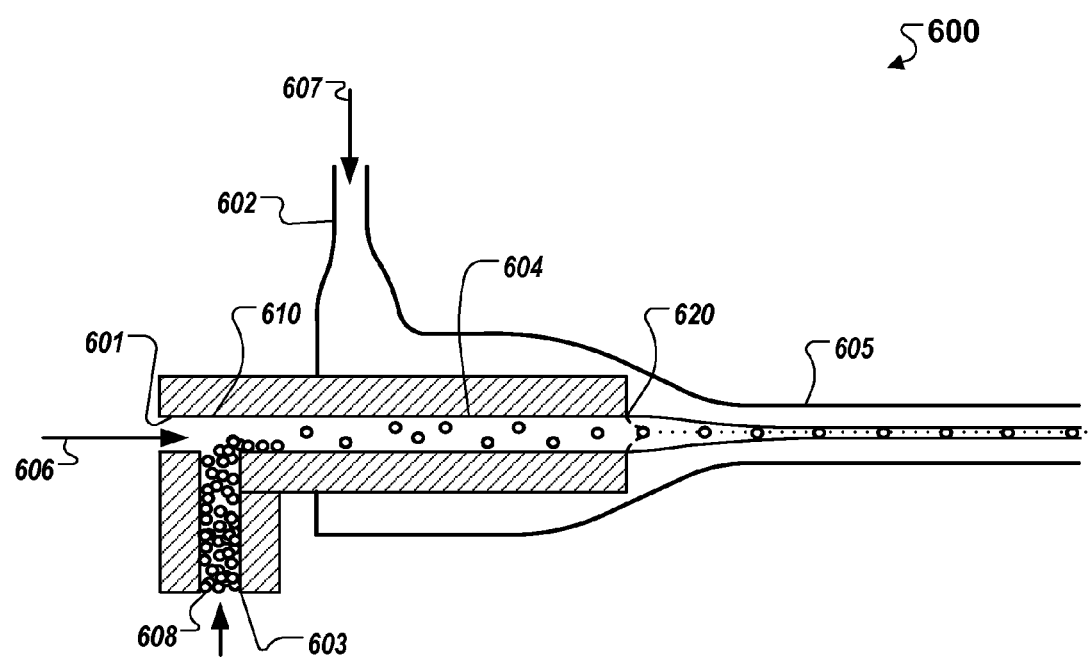
FIG. 6 is a schematic view of an exemplary circuit according to one embodiment of the present description.

Referring to FIG. 6, another example fluidic circuit 600 is depicted for controlled mixing by injecting a fluid into a concentric flow of one or more processing agents. Circuit 600 includes a first reagent channel 601, a second reagent channel 602, an inlet channel 603, a shearing channel 604, and a diffusion channel 605. Circuit 600 defines a flow path for a fluid 608 containing particulate matter, such as whole blood including suspended red and white blood cells and platelets. Fluid 608 may flow from inlet channel 603, through shearing channel 604, and into diffusion channel 605. Circuit 600 thus provides a flow path for a volume of blood 608 that can result in sustained contact between blood cells and one or more processing agents.

In an exemplary embodiment, first reagent channel 601 and inlet channel 603 intersect and are in fluid communication at a first junction 610. Fluid 608 may be sheared as it enters shearing channel 604. Second reagent channel 605 is in fluid communication with shearing channel 604 at a second junction 620 and defines a flow path for a second reagent 607. First reagent 606 and fluid 608 flowing through shearing channel 604 enter diffusion channel 605 at second junction 620, and may be injected into a central region, for example, of second reagent 607 such that fluid 608 is compressed by first and/or second reagents 606, 607. The geometry and respective flow rates of first and second reagents 606, 607, and fluid 608, may be selected as described herein to result in a thickness of fluid 608 that is similar to or less than a diameter or other dimension of particulate matter suspended in fluid 608 such that a controlled reaction may occur along diffusion channel 605.

Figure 7:
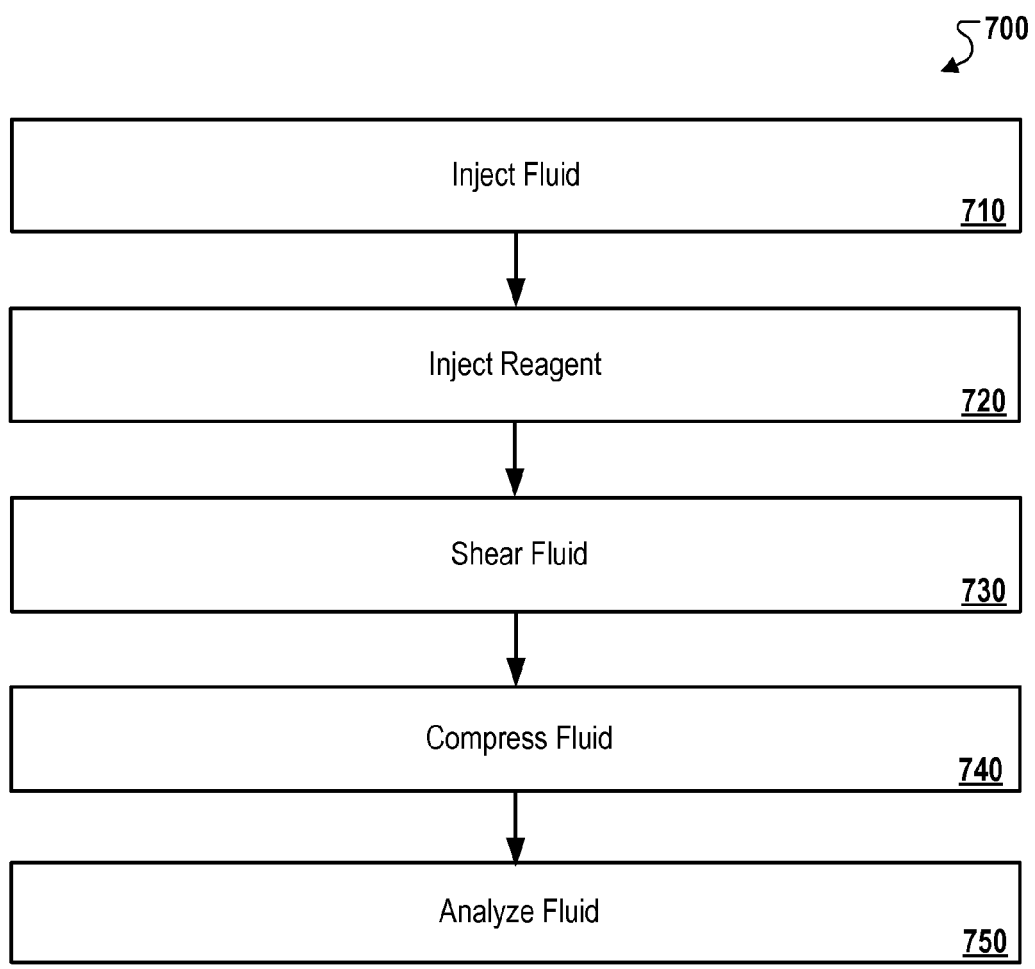
FIG. 7 is a flow chart of an exemplary method for processing a fluid.

Referring to FIG. 7, a flow chart is shown including steps of an exemplary method for processing a fluid in a circuit, such as circuit 200, 300, 400, 500, 600 for example, described herein. Step 710 includes injecting a fluid through the circuit. For example a fluid may be injected into inlet channel 203, 303, 403, 503, 603. As described herein, the fluid may be any suitable fluid for processing in a fluidic circuit, and in some exemplary embodiments, is whole blood including suspended particulate matter, (e.g. red blood cells, white blood cells, platelets).

Step 720 includes injecting one or more reagents through the circuit. For example, one or more reagents may be injected into first reagent channel 201, 301, 401, 501, 601 and/or second reagent channel 302, 402, 502, 602. In some exemplary embodiments, the circuit is provided in a disposable cartridge, and fluid and/or one or more reagents may be injected before or after the cartridge is loaded into an analyzer device (not shown). For example, a fluid may be injected into the cartridge before loading, and one or more processing agents may be injected by the analyzer device after receiving the cartridge.

The flow of one or more reagents and fluids within the circuit may be controlled due to pressure created when the reagents and/or fluids are injected. Alternatively or in addition, a desired flow may result from one or more valves that allow an analyzer device to pressurize portions of the circuit.

Step 730 includes shearing the fluid to minimize properties of a fluid that could prevent undesirable flow through the circuit, or that otherwise result in the fluid being inhomogeneous, such as aggregating properties of whole blood that may cause blood cells to clump together. Shearing may occur by any suitable device, such as interaction of the fluid with one or more of a reagent and features of the circuit, as described herein with respect to exemplary circuits 200, 300, 400, 500, 600.

Step 740 includes compressing the fluid. In some embodiments, this includes compressing the fluid to a thickness that is close to or less than a dimension of particulate matter in the fluid. In this way, particulate matter may be brought into close proximity with one or more processing agents. In some exemplary embodiments, a fluid may be compressed in part by one or more processing agents, such as interaction of the fluid with one or more of a reagent and features of the circuit, as described herein with respect to exemplary circuits 200, 300, 400, 500, 600. Fluid flow through the circuit may be controlled to direct the fluid to an analysis location where the fluid may be analyzed by any suitable analysis technique.

In various exemplary embodiments, steps 710-750 may be conducted in any suitable order or combination. For example, fluid and one or more reagents may be injected simultaneously or in sequence, and fluid may be sheared and compressed in one, two or more than two steps.

EXAMPLES

The characteristics, operation and advantages associated with various embodiments described herein may be further explained with regard to the following non-limiting examples. These examples are offered to further illustrate various embodiments and techniques. It should be understood, however, that many variations and modifications may be made while remaining within the scope of the present description.

Procedure 1: White Blood Cell Comparability

The efficacy of a processing circuit may be indicated by the quality of a white blood cell differential produced by Mie-scatter analysis of processed whole blood which has undergone a lysis reaction within the circuit. The quality of white blood cell differential is observed based on eliminating red blood cells from the signal range while maintaining white blood cell integrity such that signals generated by white blood cells provide an accurate indication of the white blood cell sub-population.

The white blood cell comparability procedure includes analysis of a set of blood samples having white blood cell sub-populations varying over the entire range of expected human white blood cell sub-populations using a processing circuit as described herein compared to a reference method, respectively. The efficacy of an example processing circuit can thus be estimated based on comparison to results of sub-population compositions observed using the reference method.

Whole blood was introduced into an inlet channel of processing circuit having the configuration shown in FIG. 4 at a rate of 0.4 μL/min, and a CDS 3200 lysis reagent, available from Clinical Diagnostic Solutions, Inc. of Plantation, Fla., was introduced into a first reagent channel at a rate of 10 μL/min. Lysis reagent was introduced into a second reagent channel at a rate of 10 μL/min, and combined with the whole blood and lysis reagent introduced at the first reagent channel. The combined streams of fluid traveled through a shearing channel and a diffusion channel to a hydrodynamic focusing circuit. The focused cells passed through a detection zone to interact with a laser beam such that cell-specific light signatures were emitted. Reflective optical elements of an analyzer device directed segments of the scattered light towards focusing lenses and a photodiode which converted the scattered lighted into a digitizeable electrical signal having a voltage pulse associated with individual cells. Peak voltage values resulting from photo-diode immunization were plotted, and sub-population analysis was performed by cluster-based partition of the scatter plots.

To obtain reference values, whole blood was introduced to a CellDyn 3200 flow cytometer, and a Mie-scatter analysis of white blood cells conducted to identify white blood cell sub-populations of the whole blood.

Example 1

Figure 8:
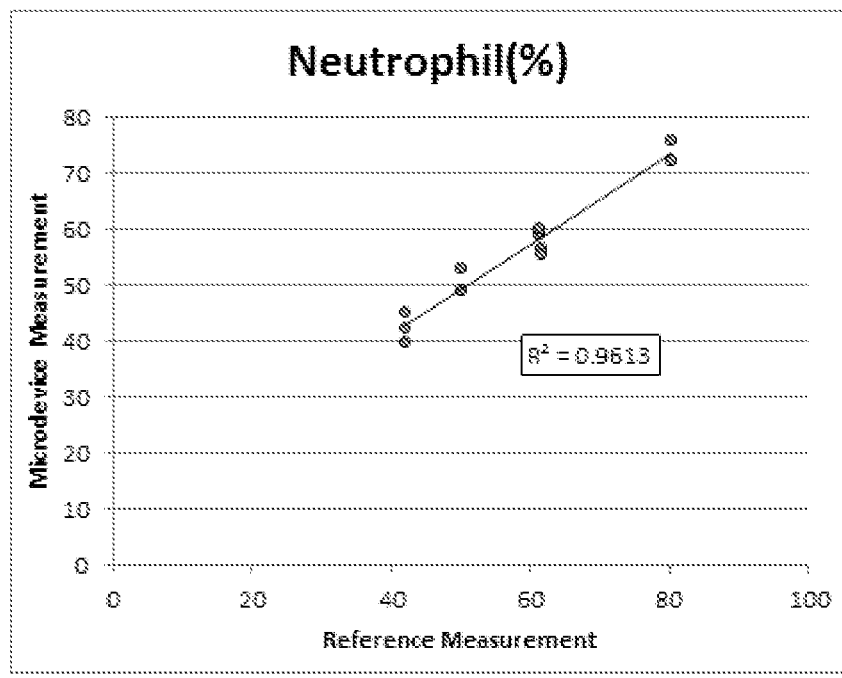
FIGS. 8-10 show example results of a WBC comparability test conducted using one embodiment of an exemplary circuit of the present description.
Figure 9:
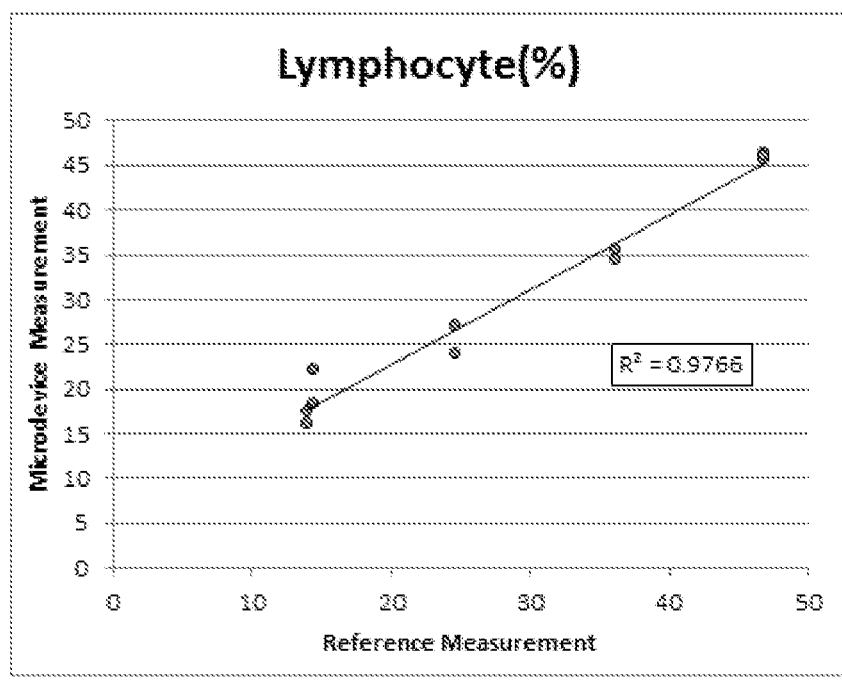
Figure 10:
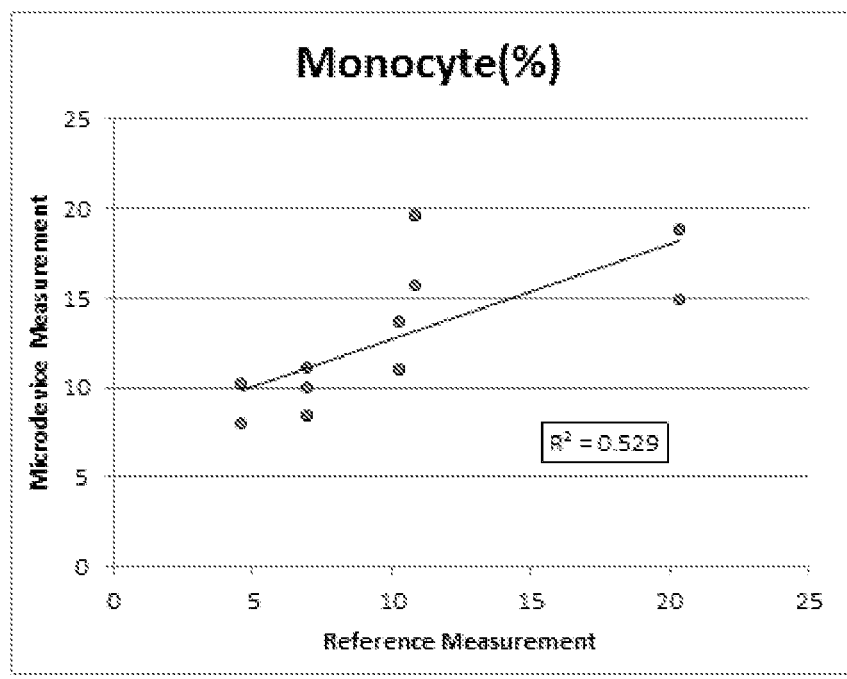

A White Blood Cell Comparability analysis was performed according to Procedure 1 using a cartridge including a processing circuit having the configuration as shown in FIG. 4 and the dimensions provided in Table 1 below. The relative accuracy of sub-population analyses obtained from the processing circuit of Example 1 relative to the CellDyn 3200 flow cytometer is reported in FIGS. 8-10 with the x-axis being the CellDyn 3200 Reference Measurement and the y-axis being the Example 1 Microdevice Measurement. FIGS. 8-10 shows that the processing circuit of Example 1 resulted in a close correlation with the results obtained by the CellDyn 3200, signifying that the while blood sample was well processed by the processing circuit.

| Processing Circuit Dimension | mm |
| --- | --- |
| Depth of First Reagent Channel | 0.15 |
| Depth of Shearing Channel | 0.15 |
| Depth of Second Reagent Channel | 0.15 |
| Depth of Diffusion Channel | 0.15 |
| Depth of Inlet Channel | 0.15 |
| Width of First Reagent Channel | 0.20 |
| Width of Shearing Channel | 0.20 |
| Width of Second Reagent Channel | 0.20 |
| Width of Diffusion Channel | 0.30 |
| Width of Inlet Channel | 0.25 |
| Length of Shearing Channel | 1.80 |
| Length of Diffusion Channel | 142 |

The foregoing detailed description and some embodiments have been given for clarity of understanding only. No unnecessary limitations are to be understood therefrom. It will be apparent to those skilled in the art that many changes can be made in the embodiments described without departing from the scope of the invention. For example, while engines are illustrated as having certain shapes and features in some embodiments, in other embodiments those shapes and features can be varied as suitable for the application. Thus, the scope of the present invention should not be limited to the exact details and structures described herein, but rather by the structures described by the language of the claims, and the equivalents of those structures. Any feature or characteristic described with respect to any of the above embodiments can be incorporated individually or in combination with any other feature or characteristic, and are presented in the above order and combinations for clarity only.

What is claimed is:
1. A fluid mixing system, comprising:
 a circuit comprising,
  a first reagent;
  a second reagent;
  a fluid comprising particulate matter having a dimension between approximately 6 μm and 24 μm;
  a fluid flowpath comprising an inlet channel, a shearing channel and a diffusion channel;
  the inlet channel defining a flow path comprising a volume of the fluid comprising particulate matter;

a first reagent channel in fluid communication with the inlet channel and defining a first reagent flow path comprising a volume of the first reagent, the inlet channel and first reagent channel configured to shear the fluid entering the shearing channel from the inlet channel at a first junction;

the shearing channel in fluid communication with the inlet channel and first reagent channel at the first junction; and the diffusion channel in fluid communication with the shearing channel at a second junction, the sheared fluid entering the diffusion channel such that the sheared fluid is compressed at least in part by the first reagent to have a thickness less than 2 times greater than the dimension of the particulate matter in the fluid, the diffusion channel defining a diffusion flow path for the first reagent to interact with, at least, a portion of the particulate matter;

and a second reagent channel in fluid communication with the shearing channel and diffusion channel at the second junction, and defining a second reagent flow path comprising a volume of the second reagent, the first reagent entering the fluid flow path at a first side of the fluid flow path at the first junction and the second reagent entering the fluid flow path at a second side of the fluid flow path at the second junction;

wherein top and bottom walls of the shearing channel and diffusion channel are coplanar, and the shearing channel has a height between the top and bottom walls proximate the first junction and the second junction that is less than or substantially equal to a width of the shearing channel.

2. The system of claim 1, wherein the first and second reagents are the same.

3. The system of claim 1, wherein the sheared fluid is compressed such that the thickness is less than the dimension of the particulate matter in the fluid such that at least a portion of the particulate matter extends beyond the thickness of the sheared fluid to contact the first reagent.

4. The system of claim 1, wherein the inlet channel has an opening at the first junction having an area between 0.005 mm² and 0.25 mm².

5. The system of claim 4, wherein the opening of the inlet channel at the first junction has a rectangular cross-section.

6. The system of claim 1, wherein the ratio of a cross-sectional area of the first reagent channel to a cross-sectional area of the inlet channel at the first junction is between 1:10 and 1:0.1.

7. The system of claim 1, wherein the ratio of a cross-sectional area of the inlet channel at the first junction to a cross-sectional area of the diffusion channel at the second junction is about 1:1.

8. The system of claim 1, wherein the first junction is configured such that the fluid is sheared along a side wall of the shearing channel.

9. The system of claim 8, wherein the side wall is oriented parallel with gravity when the circuit is positioned for use while the fluid is flowing through the inlet channel.

10. The system of claim 1, wherein the first and second junctions are separated by a distance between 0.1 mm and 5 mm.

11. The system of claim 1, wherein the shearing channel and second reagent channel form an angle between approximately 80 degrees and 190 degrees.

12. The system of claim 1, wherein the sheared fluid is surrounded on at least two opposed sides by the first and second reagents when flowing through the diffusion channel.

13. The system of claim 1, wherein the sheared fluid is surrounded on only two opposed sides by the first and second reagents when flowing through the diffusion channel.

14. The system of claim 1, wherein the fluid comprises whole blood and the particulate matter comprises blood cells.

15. The system of claim 1, further comprising:
a disposable cartridge that is configured to be inserted into an analyzer device, wherein the cartridge comprises the circuit.

16. A fluid mixing system, comprising:
a circuit comprising,
a first reagent;
a second reagent;
a fluid comprising whole blood;
a fluid flowpath comprising an inlet channel, shearing channel and diffusion channel;
the inlet channel defining an inlet flow path comprising a volume of the fluid;
a first reagent channel in fluid communication with the inlet channel and defining a first reagent flow path for a first reagent, the inlet channel and first reagent channel configured to shear the fluid entering the shearing channel from the inlet channel at a first junction at which the inlet flow path is oriented 90 degrees relative to the first reagent flow path;
the shearing channel in fluid communication with the inlet channel and first reagent channel at the first junction, wherein the fluid is sheared along a length of the shearing channel;
the second reagent channel in fluid communication with the shearing channel and defining a second reagent flow path comprising a volume of the second reagent; and
the diffusion channel in fluid communication with the shearing channel and the second reagent channel at a second junction, the sheared fluid collectable into the diffusion channel such that the sheared fluid is compressed at least in part by the second reagent to have a thickness less than 1.2 times greater than a diameter of cellular particulate matter in the fluid, the diffusion channel defining a diffusion flow path for first and second reagents to interact with, at least, a portion of the cellular particulate matter extending beyond the thickness of the sheared fluid;
wherein the ratio of the inlet channel cross-sectional area to the first reagent channel cross-sectional area at the first junction is between 1:10 and 1:0.1, wherein the first reagent enters the fluid flow path at a first side of the fluid flow path and the second reagent enters the fluid flow path at a second side of the fluid flow path; and
wherein top and bottom walls of the inlet channel, shearing channel, and diffusion channel are coplanar, and the shearing channel has a height between the top and bottom walls proximate the first junction and the second junction that is less than or substantially equal to a width of the shearing channel.

17. The system of claim 16, wherein a distance between the first and second junctions is between 0.1 mm and 5 mm.

18. The system of claim 16, wherein the first junction is configured such that the fluid is sheared along a side wall of the shearing channel.

19. The system of claim 16, wherein the inlet channel is oriented 90 degrees relative to the shearing channel.

20. The system of claim 16, wherein the shearing channel between the first and second junctions is non-parallel to the inlet channel and the diffusion channel.

21. The system of claim 1, wherein the inlet channel is oriented 90 degrees relative to the shearing channel.

22. The system of claim 1, wherein the shearing channel is non-parallel to the inlet channel and the diffusion channel between the first and second junctions.

* * * * *